US010413403B2

(12) United States Patent
Boden et al.

(10) Patent No.: US 10,413,403 B2
(45) Date of Patent: Sep. 17, 2019

(54) PROSTHETIC HEART VALVE INCLUDING SELF-REINFORCED COMPOSITE LEAFLETS

(71) Applicant: Boston Scientific SciMed, Inc., Maple Grove, MN (US)

(72) Inventors: Mark W. Boden, Harrisville, RI (US); Peter G. Edelman, Maple Grove, MN (US); Joseph Thomas Delaney, Jr., Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 107 days.

(21) Appl. No.: 15/205,098

(22) Filed: Jul. 8, 2016

(65) Prior Publication Data

US 2017/0014227 A1 Jan. 19, 2017

Related U.S. Application Data

(60) Provisional application No. 62/192,340, filed on Jul. 14, 2015.

(51) Int. Cl.
*A61F 2/24* (2006.01)
*A61L 27/20* (2006.01)

(52) U.S. Cl.
CPC .......... *A61F 2/2412* (2013.01); *A61F 2/2415* (2013.01); *A61F 2210/0076* (2013.01); *A61F 2220/0016* (2013.01); *A61F 2250/0028* (2013.01); *A61F 2250/0029* (2013.01); *A61F 2310/00011* (2013.01); *A61F 2310/00179* (2013.01); *A61L 27/20* (2013.01)

(58) Field of Classification Search
CPC .................. A61F 2/2412; A61F 2/2415; A61F 2250/0028; A61F 2250/0046; A61F 2210/0076; A61F 2220/0058; A61F 2250/0015–0019
See application file for complete search history.

(56) References Cited

U.S. PATENT DOCUMENTS

| 4,016,714 A | 4/1977 | Crandall |
| 4,340,091 A | 7/1982 | Davis et al. |
| 4,753,652 A | 6/1988 | Langer et al. |
| (Continued) | | |

FOREIGN PATENT DOCUMENTS

| CN | 1449266 | 10/2003 |
| CN | 1874799 | 12/2006 |
| (Continued) | | |

OTHER PUBLICATIONS

"International Search Report and Written Opinion," for PCT application No. PCT/US2016/050691 dated Dec. 19, 2016 (14 pages).

(Continued)

*Primary Examiner* — Yashita Sharma
(74) *Attorney, Agent, or Firm* — Pauly DeVries Smith & Deffner LLC

(57) ABSTRACT

A prosthetic heart valve leaflet is composed of a self-reinforced composite (SRC) structure that includes a first layer. The first layer can include a first plurality of fused fibers composed of a first polymeric material in which each fiber is fused to at least one adjacent fiber by a reflowed fiber domain region.

15 Claims, 6 Drawing Sheets

(56) References Cited

U.S. PATENT DOCUMENTS

| | | | |
|---|---|---|---|
| 5,296,292 A | | 3/1994 | Butters |
| 5,674,286 A | * | 10/1997 | D'Alessio et al. ............. 623/11 |
| 5,679,299 A | * | 10/1997 | Gilbert et al. ................ 264/103 |
| 5,688,597 A | | 11/1997 | Kohno |
| 5,740,051 A | | 4/1998 | Sanders, Jr. et al. |
| 6,165,215 A | | 12/2000 | Rottenberg et al. |
| 6,726,715 B2 | | 4/2004 | Sutherland |
| 6,953,332 B1 | | 10/2005 | Kurk et al. |
| 7,335,264 B2 | | 2/2008 | Austin et al. |
| 7,517,353 B2 | | 4/2009 | Weber |
| 7,521,296 B2 | | 4/2009 | Wood et al. |
| 7,615,335 B2 | | 11/2009 | Shelnut et al. |
| 7,786,670 B2 | | 8/2010 | Veres et al. |
| 7,988,900 B2 | | 8/2011 | Beith et al. |
| 8,324,290 B2 | | 12/2012 | Desai et al. |
| 8,361,144 B2 | | 1/2013 | Fish et al. |
| 8,590,747 B2 | | 11/2013 | Keller et al. |
| 8,845,580 B2 | | 9/2014 | Gellman et al. |
| 8,864,816 B2 | | 10/2014 | Flanagan et al. |
| 8,975,372 B2 | | 3/2015 | Ju et al. |
| 9,056,006 B2 | | 6/2015 | Edelman et al. |
| 9,074,318 B2 | | 7/2015 | Chou et al. |
| 9,255,929 B2 | | 2/2016 | Jiang et al. |
| 9,481,949 B2 | | 11/2016 | Zhang et al. |
| 9,554,900 B2 | | 1/2017 | Bruchman et al. |
| 9,737,400 B2 | | 8/2017 | Fish et al. |
| 9,814,572 B2 | | 11/2017 | Edelman et al. |
| 9,944,529 B2 | | 4/2018 | Zhang et al. |
| 10,195,023 B2 | | 2/2019 | Wrobel |
| 2001/0025196 A1 | | 9/2001 | Chinn et al. |
| 2002/0082689 A1 | | 6/2002 | Chinn et al. |
| 2003/0055496 A1 | | 3/2003 | Cai et al. |
| 2003/0078652 A1 | | 4/2003 | Sutherland et al. |
| 2003/0097175 A1 | | 5/2003 | O'connor et al. |
| 2003/0171802 A1 | | 9/2003 | Wilder et al. |
| 2003/0183982 A1 | | 10/2003 | Jansen et al. |
| 2004/0015233 A1 | | 1/2004 | Jansen et al. |
| 2004/0022939 A1 | | 2/2004 | Kim et al. |
| 2005/0228486 A1 | | 10/2005 | Flagle et al. |
| 2006/0190074 A1 | | 8/2006 | Hill et al. |
| 2007/0118210 A1 | | 5/2007 | Pinchuk et al. |
| 2007/0144124 A1 | | 6/2007 | Schewe et al. |
| 2007/0232169 A1 | | 10/2007 | Strickler et al. |
| 2007/0254005 A1 | | 11/2007 | Pathak et al. |
| 2008/0045420 A1 | | 2/2008 | Karagianni et al. |
| 2009/0041978 A1 | | 2/2009 | Sogard et al. |
| 2009/0054969 A1 | | 2/2009 | Salahieh et al. |
| 2009/0117334 A1 | | 5/2009 | Sogard et al. |
| 2009/0149673 A1 | | 6/2009 | Zhang et al. |
| 2009/0155335 A1 | | 6/2009 | Oshaughnessey et al. |
| 2009/0324679 A1 | | 12/2009 | Ippoliti et al. |
| 2010/0023104 A1 | | 1/2010 | Desai et al. |
| 2010/0179298 A1 | | 7/2010 | Faust et al. |
| 2010/0249922 A1 | | 9/2010 | Li et al. |
| 2011/0022160 A1 | | 1/2011 | Flanagan et al. |
| 2011/0208299 A1 | | 8/2011 | Marissen et al. |
| 2011/0305898 A1 | | 12/2011 | Zhang et al. |
| 2012/0258313 A1 | | 10/2012 | Wen et al. |
| 2012/0290082 A1 | | 11/2012 | Quint et al. |
| 2013/0150957 A1 | | 6/2013 | Weber et al. |
| 2013/0211508 A1 | | 8/2013 | Lane et al. |
| 2013/0274874 A1 | | 10/2013 | Hammer et al. |
| 2014/0005771 A1 | | 1/2014 | Braido et al. |
| 2014/0005772 A1 | | 1/2014 | Edelman et al. |
| 2014/0018440 A1 | | 1/2014 | Boden et al. |
| 2014/0088716 A1 | | 3/2014 | Zubok et al. |
| 2014/0163671 A1 | | 6/2014 | Bruchman et al. |
| 2014/0180402 A1 | | 6/2014 | Bruchman et al. |
| 2014/0322512 A1 | | 10/2014 | Pham et al. |
| 2015/0005869 A1 | | 1/2015 | Soletti et al. |
| 2015/0182332 A1 | | 7/2015 | Edelman et al. |
| 2015/0265392 A1 | | 9/2015 | Flanagan et al. |
| 2016/0296322 A1 | | 10/2016 | Edelman et al. |
| 2016/0296323 A1 | | 10/2016 | Wulfman et al. |
| 2016/0296325 A1 | | 10/2016 | Edelman et al. |
| 2017/0000610 A1 | | 1/2017 | Eppihimer et al. |
| 2017/0071729 A1 | | 3/2017 | Wrobel |
| 2017/0156854 A1 | | 6/2017 | Hammer |
| 2017/0231758 A1 | | 8/2017 | Bruchman et al. |
| 2017/0266350 A1 | | 9/2017 | Jiang et al. |
| 2017/0333185 A1 | | 11/2017 | Weber et al. |
| 2018/0049869 A1 | | 2/2018 | Edelman et al. |
| 2018/0303972 A1 | | 10/2018 | Delaney, Jr. et al. |

FOREIGN PATENT DOCUMENTS

| | | |
|---|---|---|
| CN | 101437663 | 5/2009 |
| CN | 101505723 | 8/2009 |
| CN | 101690683 | 4/2010 |
| CN | 103628147 | 3/2014 |
| CN | 104203151 | 12/2014 |
| CN | 104780952 | 7/2015 |
| JP | H0654868 | 3/1994 |
| WO | 0224119 | 3/2002 |
| WO | 02074201 | 9/2002 |
| WO | 2005039664 | 5/2005 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |
| WO | 2018200378 | 11/2018 |

OTHER PUBLICATIONS

Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).

"Non-Final Office Action," for U.S. Appl. No. 14/656,044 dated Mar. 17, 2017 (34 pages).

"Response to Communication Pursuant to Article 94(3) EPC," for European Patent Application No. 13739321.1 filed with the EPO Jan. 2, 2017 (37 pages).

"Response to Final Office Action," for U.S. Appl. No. 14/656,044, dated Sep. 9, 2016 and filed with the USPTO Dec. 8, 2016 (9 pages).

Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).

"Communication Pursuant to Article 94(3) EPC," for European Patent Application No. 13739321.1 dated Sep. 8, 2016 (4 pages).

"Final Office Action," for U.S. Appl. No. 14/656,044 dated Sep. 9, 2016 (17 pages).

"International Search Report and Written Opinion," for PCT Application No. PCT/US2016/041757 dated Oct. 12, 2016 (12 pages).

"International Search Report and Written Opinion," for PCT/US2016/039808 dated Sep. 26, 2016 (11 pages).

"Second Office Action," for Chinese Patent Application No. 201380044842.0 dated Aug. 12, 2016 (16 pages) with summary.

Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).

Fabreguette, et al., "X-ray mirrors on flexible polymer substrates fabricated by atomic layer deposition," Thin Solid Films 515: 7177-7180 (2007), 5 pages.

Fabreguette, Francois H. et al., "Ultrahigh x-ray reflectivity from W/Al2O3 multilayers fabricated using atomic layer deposition," Applied Physics Letters 88: 013166 (2006), 3 pages.

"File History," for U.S. Appl. No. 13/932,968.

(56) References Cited

OTHER PUBLICATIONS

"Final Office Action," for U.S. Appl. No. 15/193,794 dated May 23, 2018 (12 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).
Hass, D. D. et al., "Reactive vapor deposition of metal oxide coatings," Surface and Coatings Technology 146-147 (2001) 85-93, 9 pages.
"International Search Report and Written Opinion," for PCT Application No. PCT/US2017/032656 dated Jul. 21, 2017 (16 pages).
Jen, Shih-Hui et al., "Critical tensile and compressive strains for cracking of al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185 (11 pages).
"Non-Final Office Action," for U.S. Appl. No. 15/082,239 dated May 16, 2018 (34 pages).
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Non-Final Office Action," for U.S. Appl. No. 15/257,211, dated Apr. 10, 2018 and filed with the USPTO Jun. 18, 2018 (10 pages).
"Resposne to Non-Final Office Action," for U.S. Appl. No. 15/082,239, dated May 16, 2018 and filed with the USPTO Jun. 19, 2018 (13 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967 (13 pages).
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"Decision of Final Rejection," for China Patent Application No. 201380044842.0, dated Apr. 7, 2017 (18 pages) with Summary.
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"International Preliminary Report on Patentability," for PCT Application No. PCT/US2016/050691 dated Mar. 29, 2018 (9 pages).
"Non-Final Office Action," for U.S. Appl. No. 15/193,794 dated Mar. 14, 2018 (14 pages).
"Non-Final Office Action," for U.S. Appl. No. 15/193,794 dated Nov. 6, 2017 (32 pages).
"Non-Final Office Action," for U.S. Appl. No. 15/257,211 dated Apr. 10, 2018 (39 pages).
"Notification of Patent Reexamination," for Chinese Patent Application No. 201380044842.0 dated Feb. 7, 2018 (8 pages).
"Response to Non-Final Office Action," for U.S. Appl. No. 14/656,044 dated Mar. 17, 2017 and filed with the USPTO Jun. 8, 2017 (11 pages).
"Response to Non-Final Office Action," for U.S. Appl. No. 15/193,794, dated Mar. 14, 2018 and filed with the USPTO Apr. 16, 2018 (8 pages).
"Response to Non-Final Office Action," for U.S. Appl. No. 15/193,794, dated Nov. 6, 2017 and filed with the USPTO Feb. 13, 2018 (7 pages).
Final Office Action for U.S. Appl. No. 15/257,211 dated Jul. 26, 2018 (13 pages).
International Search Report and Written Opinion for PCT Application No. PCT/US2018/028864 dated Jul. 30, 2018 (10 pages).
Madhusha, "Difference between Fluorine and Fluoride," Aug. 9, 2017, PEDIAA.com, pp. 1-8. URL <http://pediaa.com/difference-between-fluorine-and-fluoride/> (8 pages).
Non-Final Office Action for U.S. Appl. No. 15/082,293 dated Jul. 11, 2018 (41 pages).
Non-Final Office Action for U.S. Appl. No. 15/595,176 dated Aug. 27, 2018 (30 pages).
Response to Communication Pursuant to Rules 161(1) and 162 EPC for European Patent Application No. 16736720.0 filed with the EPO Jul. 12, 2018 (12 pages).
Response to Final Office Action for U.S. Appl. No. 15/193,794, dated May 23, 2018 and filed with the USPTO Jul. 17, 2018 (10 pages).
Response to Final Rejection dated Jul. 26, 2018, for U.S. Appl. No. 15/257,211, submitted via EFS-Web on Aug. 9, 2018.
Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).
Alferiev, Ivan et al., "Prevention of polyurethane valve cusp calcification with covalently attached bisphosphonate diethylamino moieties," J Biomed Mater Res 66A: 385-395, 2003 (11 pages).
Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).
Barkoula, Nektaria-Marianthi et al., "Processing of Single Polymer Composites Using the Concept of Constrained Fibers," Polymer Composites, 2005, 26: p. 114-120 (7 pages).
Bastiaansen, Cees W. et al., "Melting Behavior of Gelspun-Drawn Polyolefins," Makromol. Chem., Macromol. Symp., 1989. 28: p. 73-84 (12 pages).
Bates, Frank S. et al., "Multiblock Polymers: Panacea or Pandora's Box?," Science, 2012, 336:434-440 (7 pages).
Bernacca, Gillian M. et al., "Mechanical and morphological study of biostable polyurethane heart valve leaflets explanted from sheep," J Biomed Mater Res 61:138-145, 2002 (8 pages).
Bhattacharyya, D. et al., "Polyamide 6 single polymer composites," eXPRESS Polym. Lett., 2009. 3(8): p. 525-532 (8 pages).
Cacciola, G. et al., "A synthetic fiber-reinforced stentless heart valve," Journal of Biomechanics, Jan. 1, 2000 (Jan. 1, 2000), pp. 653-658, XP055284947, Retrieved from the Internet: URL:http://ac.els-cdn.com/ (6 pages).
Cacciola, G. et al., "A three-dimesional mechanical analysis of a stentless fibre-reinforced aortic valve prosthesis," Journal of Biomechanics, Jan. 1, 2000 (Jan. 1, 2000), pp. 521-530, XP055284955, Retrieved from the Internet: URL:http://ac.els-cdn.com/ (10 pages).
Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).
Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

(56) References Cited

OTHER PUBLICATIONS

"Communication Pursuant to Rules 161(1) and 162 EPC," for EP Patent Application No. 13739321.1-1455 dated Feb. 18, 2015 (2 pages).
De Yoreo, James J. et al., "Principles of Crystal Nucleation and Growth," Biomineralization, Mineral Soc. Am., Washington, DC, 2003, pp. 57-93 (37 pages).
Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
"First Office Action," for Chinese Patent Application No. 201380044842.0 dated Dec. 18, 2015 (15 pages) with English Translation.
Gallocher, "Durability Assessment of Polymer Trileaflet Heart Valves," (2007). FIU Electronic Theses and Dissertations. Paper 54 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," for International Application No. PCT/US2013/048976 dated Jan. 6, 2015 (9 pages).
"International Search Report & Written Opinion," for International Application No. PCT/US2013/048976, dated Nov. 19, 2013 (20 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).

Kaflon-Cohen, Estelle et al., "Microstructure and nematic transition in thermotropic liquid crystalline fibers and their single polymer composites," Polym. Adv. Technol., 2007. 18(9): p. 771-779 (9 pages).
Kalejs, et al., "St. Jude Epic heart valve bioprostheses versus native humand and porcine aortic valves—comparison of mechanical properties," Interactive Cardiovascular and Thoracic Surgery 8 (2009) 553-557 (5 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785 (28 pages).
Matabola, K. P. et al., "Single polymer composites: a review," Journal of Materials Science, 2009. 44(23): p. 6213-6222 (10 pages).
Medeiros Araujo, Thiago et al., "Liquid crystalline single-polymer short-fibers composites," Composite Interfaces, 2013. 20(4): p. 287-298 (12 pages).
"Non-Final Office Action," for U.S. Appl. No. 14/656,044, dated May 20, 2016 (20 pages).
Ohri, Rachit et al., "Hyaluronic acid grafting mitigates calcification of glutaraldehyde-fixed bovine pericardium," J Biomed Mater Res 70A: 328-334, 2004 (7 pages).
"Response to Non-Final Office Action," for U.S. Appl. No. 14/656,044, dated May 20, 2016 and filed with the USPTO Aug. 9, 2016 (11 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
Sun, Xiaoli et al., "α and β Interfacial Structures of the iPP/PET Matrix/Fiber Systems," Macromolecules, 2007. 40(23): p. 8244-8249 (6 pages).
Vesely, et al., "Micromechanics of the fibrosa and the ventricularis in aortic valve leaflets," J Biomech. 1992 25(1):101-113 (12 pages).
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (10 pages).

(56) References Cited

OTHER PUBLICATIONS

Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
Final Office Action for U.S. Appl. No. 15/797,394 dated Jan. 30, 2019 (12 pages).
First Office Action for Chinese Patent Application No. 201680053293.7 dated Mar. 5, 2019 (5 pages) No English Translation.
Non-Final Office Action for U.S. Appl. No. 15/082,239 dated Apr. 4, 2019 (12 pages).
Non-Final Office Action for U.S. Appl. No. 15/193,794 dated Jan. 29, 2019 (25 pages).
Notice of Allowance for U.S. Appl. No. 15/082,293 dated Jan. 17, 2019 (12 pages).
Notice of Allowance for U.S. Appl. No. 15/082,382 dated Jan. 25, 2019 (14 pages).
Notice of Allowance for U.S. Appl. No. 15/959,176 dated Mar. 21, 2019 (13 pages).
Response to Communication Pursuant to Rules 161(1) and 162 EPC for European Patent Application No. 17725140.2 filed Apr. 2, 2019 (9 pages).
Response to Final Rejection dated Oct. 12, 2018, and Advisory Action dated Jan. 22, 2019, for U.S. Appl. No. 15/082,239, submitted via EFS-Web on Feb. 12, 2019, 7 pages.
Third Office Action for Chinese Patent Application No. 201380044842.0 dated Dec. 29, 2018 (12 pages), with English translation.
"Final Office Action," for U.S. Appl. No. 15/082,239 dated Oct. 12, 2018 (19 pages).
"First Office Action," for Chinese Patent Application No. 20160036250.8 dated Nov. 2, 2018 (11 pages) with English Summary.
"First Office Action," for Chinese Patent Application No. 201680018700.0 dated Nov. 2, 2018 (12 pages) with English Summary.
"International Preliminary Report on Patentability," for PCT Application No. PCT/US2017/032656 dated Nov. 29, 2018 (7 pages).
"Non-Final Office Action," for U.S. Appl. No. 15/082,382 dated Sep. 19, 2018 (8 pages).
"Non-Final Office Action," for U.S. Appl. No. 15/797,394 dated Sep. 26, 2018 (39 pages).
"Response to Communication Pursuant to Rules 161(1) and 162 EPC," for European Patent Application No. 16766455.6 filed Dec. 4, 2018 (9 pages).
"Response to Final Rejection," dated Oct. 12, 2018, for U.S. Appl. No. 15/082,239, submitted via EFS-Web on Dec. 17, 2018, 9 pages.
"Response to Non-Final Rejection," dated Aug. 27, 2018, for U.S. Appl. No. 15/595,176, submitted via EFS-Web on Nov. 26, 2018, 6 pages.
"Response to Non-Final Rejection," dated Jul. 11, 2018, for U.S. Appl. No. 15/028,293, submitted via EFS-Web on Oct. 11, 2018, 12 pages.
"Response to Non-Final Rejection," dated Sep. 19, 2018, for U.S. Appl. No. 15/082,382, submitted via EFS-Web on Dec. 18, 2018, 6 pages.
"Response to Non-Final Rejection," dated Sep. 26, 2018, for U.S. Appl. No. 15/797,394, submitted via EFS-Web on Dec. 19, 2018, 9 pages.

\* cited by examiner

PROSTHETIC HEART VALVE INCLUDING SELF-REINFORCED COMPOSITE LEAFLETS

This application claims the benefit of U.S. Provisional Application No. 62/192,340 filed Jul. 14, 2015, the contents of which are herein incorporated by reference.

TECHNICAL FIELD

The present invention relates to prosthetic heart valves composed of self-reinforced composites and methods related thereto.

BACKGROUND

More than 250,000 heart valves are replaced worldwide each year due to structural defects such as valve stenosis that may lead to regurgitation. Valve stenosis is a condition where a heart valve is not able to fully open when blood is pumped through the heart because the heart valve leaflets are too stiff or fused together. Valve stenosis creates a narrowed opening that stresses the heart, which in turn can cause fatigue and dizziness in a patient. Regurgitation, which is a backward flow of blood, can reduce efficiency of the heart pumping blood and also cause a patient to experience fatigue as well as shortness of breath.

Long term implants, such as prosthetic heart valves, can be used for diseased heart valve replacement. Some prosthetic heart valves are made entirely of synthetic materials, while others are made of a combination of synthetic materials and animal tissues, for example, bovine or porcine pericardium. Prosthetic heart valves made of synthetic materials can have inadequate chemical stability or cause an undesirable biological response in a patient while prosthetic heart valves made of animal tissue are often vulnerable to structural deterioration caused by calcification that results in the narrowing of the valve orifice and/or cusp tearing. There is a need for a prosthetic heart valve that can have long term chemical stability and mechanical properties that can mimic a native heart valve.

SUMMARY

Disclosed herein are various embodiments of prosthetic heart valve devices that include self-reinforced composite leaflets and methods related thereto.

In Example 1, a prosthetic heart valve leaflet has a self-reinforced composite (SRC) structure that includes a first layer. The first layer can include a first plurality of fused fibers composed of a first polymeric material. Each fiber of the first layer can be fused to at least one adjacent fiber by a reflowed fiber domain region.

In Example 2, the prosthetic heart valve leaflet of Example 1, further including a second layer that has a second plurality of fused fibers composed of a second polymeric material in which each fiber can be fused to at least one adjacent fiber by a reflowed fiber domain region In Example 3, the prosthetic heart valve leaflet of Example 2, wherein the first plurality of fused fibers and the second plurality of fused fibers are generally aligned in at least two directions such that the first plurality of the fused fibers are oriented at a first predetermined fiber angle relative to the second plurality of fused fibers.

In Example 4, the prosthetic heart valve leaflet of any one of Examples 1-3, wherein the first plurality of fused fibers are generally aligned in a direction defining a first longitudinal axis, the first longitudinal axis being oriented at an angle relative to a free edge of the prosthetic heart valve leaflet.

In Example 5, the prosthetic heart valve leaflet of one of Examples 2-4, wherein the first layer is disposed adjacent to the second layer.

In Example 6, the prosthetic heart valve leaflet of any one of Examples 2-4, wherein the first and second plurality of fused fibers are generally aligned relative to each other to form a biaxial orientation within the SRC structure.

In Example 7, the prosthetic heart valve leaflet of any one of Examples 3-5, wherein the predetermined fiber angle is an orthogonal angle.

In Example 8, the prosthetic heart valve leaflet of any one of Examples 3-5, wherein the predetermined fiber angle is one of 10, 20, 30, 40, 45, 50, 60, 70, or 80 degrees.

In Example 9, the prosthetic heart valve leaflet of any one of Examples 1-8, wherein the SRC structure includes additional layers to form a three-, four-, or a five-composite-layered SRC structure.

In Example 10, the prosthetic heart valve leaflet of Example 9, wherein the three-, four- or five-composite-layered of the SRC structure forms a triaxial, a quadaxial or a quinaxial orientation, respectively.

In Example 11, the prosthetic heart valve leaflet of any one of Examples 1-10, wherein each fiber of the first plurality of fused fibers includes an aligned polymer crystal orientation that is generally parallel with the first longitudinal axis.

In Example 12, the prosthetic heart valve leaflet of any one of Examples 1-8, wherein the first polymeric material is a polyurethane, a polyisobutylene urethane (PIB-PUR) copolymer, a polyamide, a polyimide, a polycarbonate, a polyester, a polyetherether ketone, or a fluorinated polyolefin.

In Example 13, the prosthetic heart valve leaflet of any one of Examples 2-10, wherein the first and second polymeric materials are different materials.

In Example 14, the prosthetic heart valve leaflet of Example 13, wherein the first polymeric material is a high-melt-temperature polyurethane and second polymeric material is a low-melt-temperature polyurethane.

In Example 15, the prosthetic heart valve leaflet of any one of Examples 2-10, wherein the first layer at least partially overlaps the second layer.

In Example 16, the prosthetic heart valve leaflet of Example 2, wherein at least a portion of the first layer is fused to at least a portion of the second layer.

In Example 17, the prosthetic heart valve leaflet of Example 1, wherein each fiber of the first plurality of fibers has a generally square, oval, or hexagonal cross-sectional shape.

In Example 18, a method forming a prosthetic heart valve leaflet, the method including compressing and heating a fibrous structure including a plurality of fibers made of a polymeric material to a predetermined temperature for a predetermined amount of time to form a self-reinforced composite (SRC) structure in which portions of the plurality of fibers are fused together.

In Example 19, the method of Example 18, wherein the fibrous structure includes a plurality of fibers each having an original fiber diameter ranging from about 10 nm to about 50,000 nm (or 50 micrometers) prior to the compressing and heating.

In Example 20, the method of Example 18, wherein the predetermined temperature ranges from a glass transition temperature (Tg) and a melting temperature (Tm); and a compressional strain of between 0 and 50 is applied to the plurality of fibers of the fibrous structure during the compressing and the heating.

BRIEF DESCRIPTION OF THE DRAWINGS

FIG. 6A provides an illustration of a fiber composed of random amorphous domains. FIG. 6B provides an illustration of a fiber composed of aligned crystalline domains.

DETAILED DESCRIPTION

Figure 1:
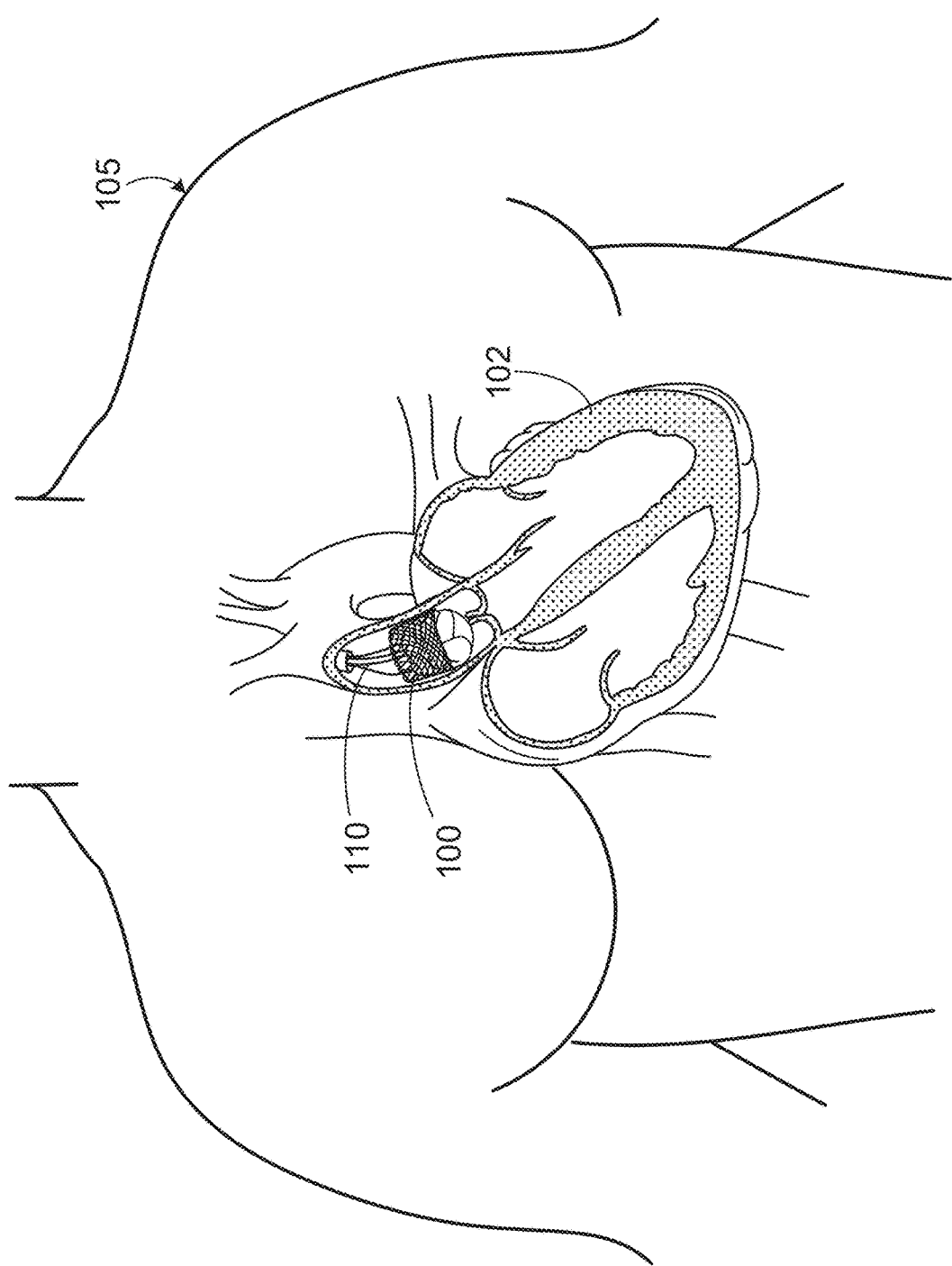
FIG. 1 is an illustration of an exemplary prosthetic heart valve provided herein within a human anatomy.

FIG. 1 shows an illustration of a prosthetic heart valve 100 provided herein within a heart 102 of a human body 105. The human body 105 has four heart valves: a pulmonary valve, a tricuspid valve, an aortic valve and a mitral valve. The purpose of the heart valves is to allow blood to flow through the heart and from the heart into the major blood vessels connected to the heart, such as the aorta and pulmonary artery. Prosthetic heart valve 100 of FIG. 1 is an aortic prosthetic heart valve that can be delivered using a transcatheter aortic valve replacement (TAVR) procedure (which is also described as percutaneous aortic valve replacement (PAVR) or transcatheter aortic valve implantation (TAVI)), which involves the use of a deployment device 110 (which can also be referred to as a delivery catheter or delivery system) placed through blood vessels from a femoral, subclavian, or direct aortic incision. Deployment device 110 can deliver prosthetic heart valve 100 to the desired location within the anatomy, and release implantable heart valve 100 at an implantation site. Although FIG. 1 shows an aortic prosthetic heart valve, it should be appreciated by one skilled in the art that prosthetic heart valve 100 can be another type of heart valve (e.g., a mitral valve or a tricuspid valve), in some cases. In some cases, the prosthetic heart valve provided herein can be generally applicable to other types of valves within the body.

Figure 2:
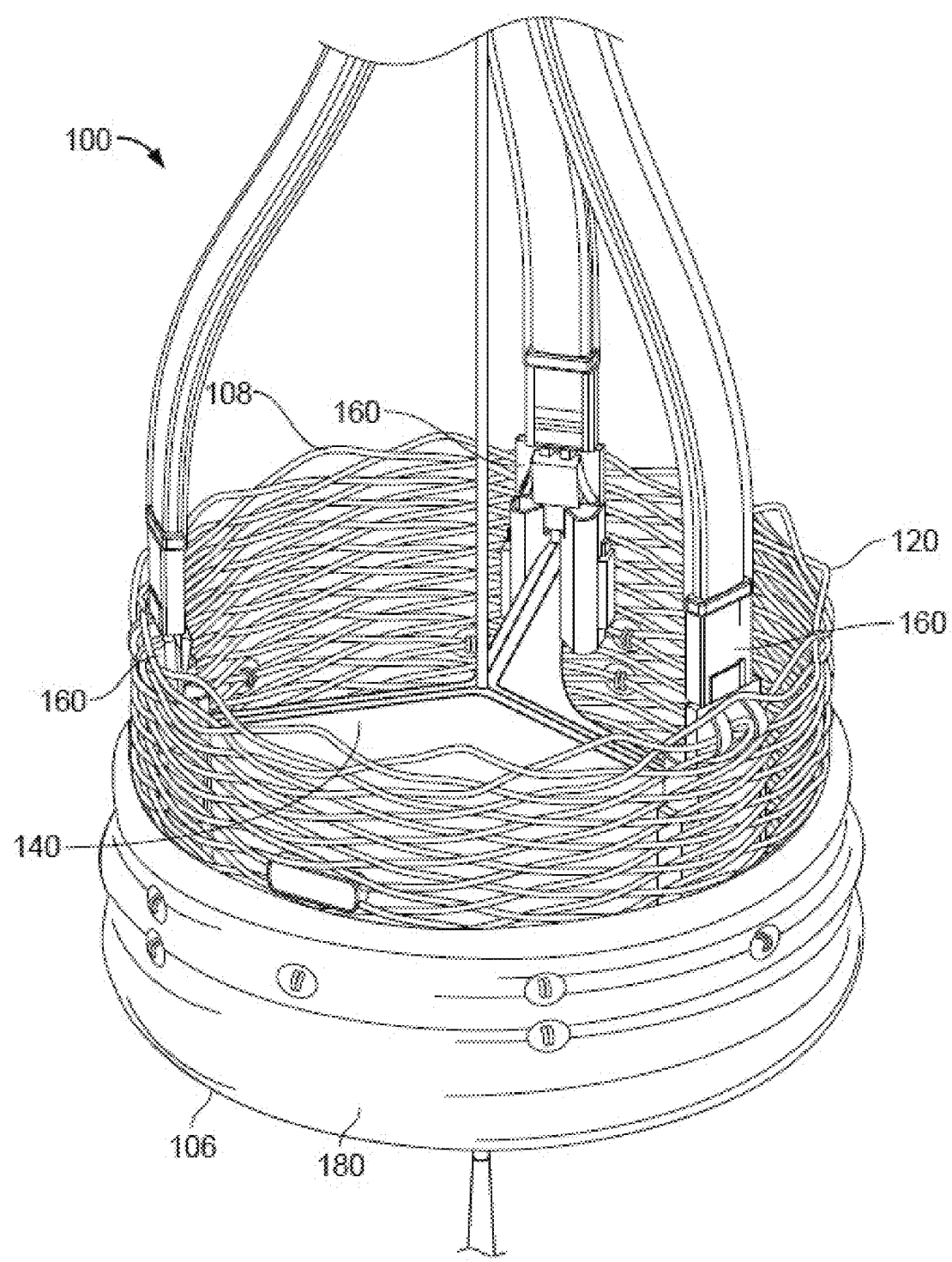
FIG. 2 is an enlarged view of the prosthetic heart valve of FIG. 1.

FIG. 2 provides a close up view of the prosthetic heart valve 100 of FIG. 1, which has an inflow end 106 and an outlet end 108. Prosthetic heart valve 100 has a substantially tubular body 120, a plurality of leaflets 140, anchor elements 160, and a tubular seal 180. Tubular body 120 can be a radially expandable member, e.g. annular frame or stent, having an annular cavity. As shown in FIG. 2, the heart valve 100 can have three heart valve leaflets 140 coupled to the tubular body 120 within the annular cavity. Three anchor elements 160 positioned within the annular cavity of the tubular body 120 can each secure the heart valve leaflets to the tubular body 120. Each anchor element 160 can be coupled to the tubular body 120 with an anchoring element and coupled to the leaflets with a clamping element. The tubular seal 180 can be disposed about at least a portion of the tubular body 120. In particular, the tubular seal can have an inflow end portion secured to bottom edges of the plurality of leaflets at the inflow end 106 and have an outflow end portion disposed about an outer surface of the tubular body 120 at the outflow end 108 to restrict blood flow around the leaflets.

Prosthetic heart valve 100 can be made of various materials. In some cases, at least a portion of the prosthetic heart valve 100, for example, the leaflets 140 or a portion of the tubular body 120, can be made of various synthetic materials. In some cases, the prosthetic heart valve 100 can be made entirely of synthetic materials. The synthetic materials of the prosthetic heart valve 100 can include polymeric materials, metals, ceramics, and combinations thereof. In some cases, synthetic materials of the prosthetic heart valve 100 can include composite structures. In some cases, as will be discussed in further sections, a prosthetic heart valve can be made of a specific type of composite such as a self-reinforced composite (SRC) structure provided herein.

In use, prosthetic heart valve 100 is implanted (e.g., surgically or through transcatheter delivery) in a mammalian heart. The edge portions of the polymeric leaflets 140 move into coaptation with one another to substantially restrict fluid from flowing past prosthetic heart valve 100 in a closed position. The edge portions of the leaflets 140 move away from one another to an open position, permitting fluid to flow past prosthetic heart valve 100. Movement of the leaflets between the closed and open positions can substantially approximate the hemodynamic performance of a healthy natural valve.

Figure 3:
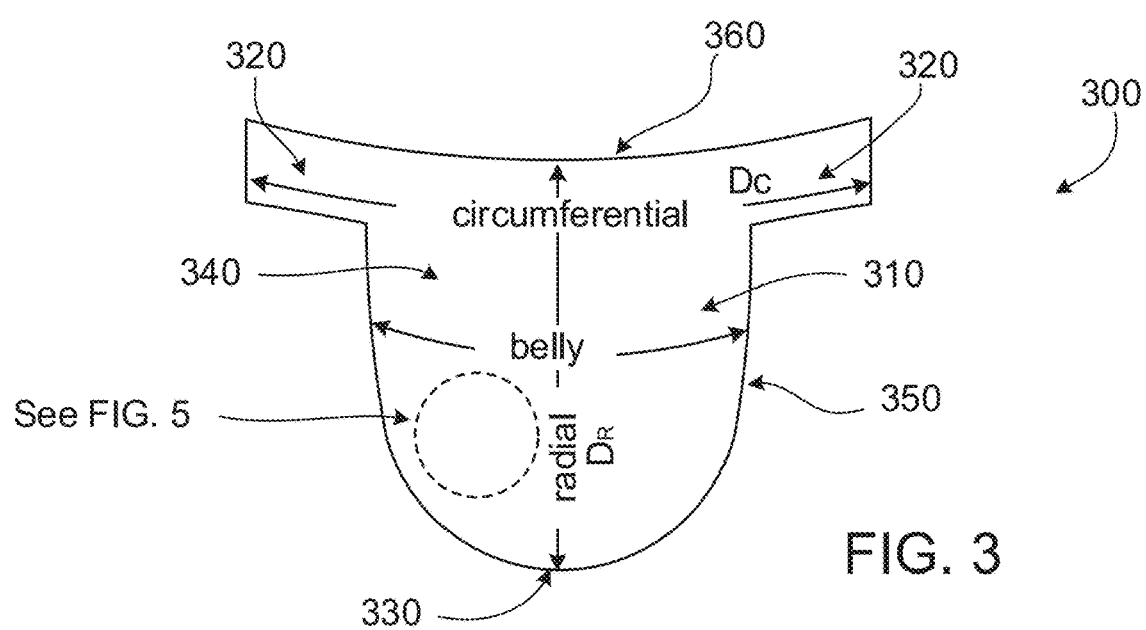
FIG. 3 is a plan view of an exemplary leaflet provided herein including a self-reinforced composite (SRC) structure.

FIG. 3 shows an example of a prosthetic heart valve leaflet 300 provided herein. As shown, leaflet 300 can include a body portion 310 (or belly region of the leaflet) and two sleeve portions 320 that extend outwardly from the body portion 310. In some cases, the body portion 310 has a bottom edge 330, a first side edge 340, a second side edge 350, and a free edge 360. Leaflet 300 further includes a front side (i.e., the side that blood flows toward), a back side (i.e., the side that blood flows away from). The bottom edge 330 and side edges 340, 350 of the body portion 310 can be shaped for suturing and for forming a leaflet profile similar to a native valve. The sleeve portions 320 can be shaped to be compatible with anchor elements, such as anchor elements 160 of FIG. 2.

As the prosthetic heart valve opens and closes, each leaflet flexes between the open and closed position. Tensile and flexural strain on each leaflet can change depending on its position. As such, the leaflet 300 can elongate in various directions as the valve opens and closes. For instance, leaflet 300 can elongate along the body portion 310 and the sleeve portions 320 in a radial direction $D_R$, or a circumferential direction $D_C$, or both. The radial direction $D_R$ of a leaflet in a heart valve can extend radially inwardly or outwardly, e.g., a radial direction can extend from the center of the heart valve along a free edge of a valve leaflet to a commissure. The circumferential direction $D_C$ can extend along a circumference of a heart valve, e.g., an inner circumference of the tubular body 120 of FIG. 2. As shown in FIG. 3, the radial direction $D_R$ can extend from the free edge 360 to the bottom edge 330 of the leaflet. A circumferential direction $D_C$ extends in a direction that is generally orthogonal to the radial direction $D_R$. More specifically, the circumferential direction $D_C$ can extend from one side edge to the opposite side edge of the sleeve portion. The circumferential direction $D_C$ can also extend from one side of the body portion (e.g., the first side edge 340) to an opposite side of the body portion (e.g., the second side edge 350), which can be described as a circumferential direction $D_C$ in the belly region of the leaflet 300. In some cases, the leaflet 300 can elongate in a direction having an angle that is oblique relative to the radial and circumferential directions.

The prosthetic heart valves provided herein can be made of self-reinforced composite (SRC) structures (which can also be described as self-fused composites). The "self-reinforced composite" structure is a composite material composed of a plurality of fused fibers in which an outer surface of each fused fiber is fused to at least one adjacent fiber by a reflowed fiber domain region. In some cases, the SRC structures can be made of fibers of a single polymer. In some cases, the SRC structures can be made of composite fibers, e.g., fibers having a core and a sheath, in which the sheath of the composite fiber is a different material than the core. Self-reinforced composite structures provided herein can be used to form at least a portion of a heart valve device, such as a heart valve leaflet or a portion of a heart valve leaflet.

Figure 4:
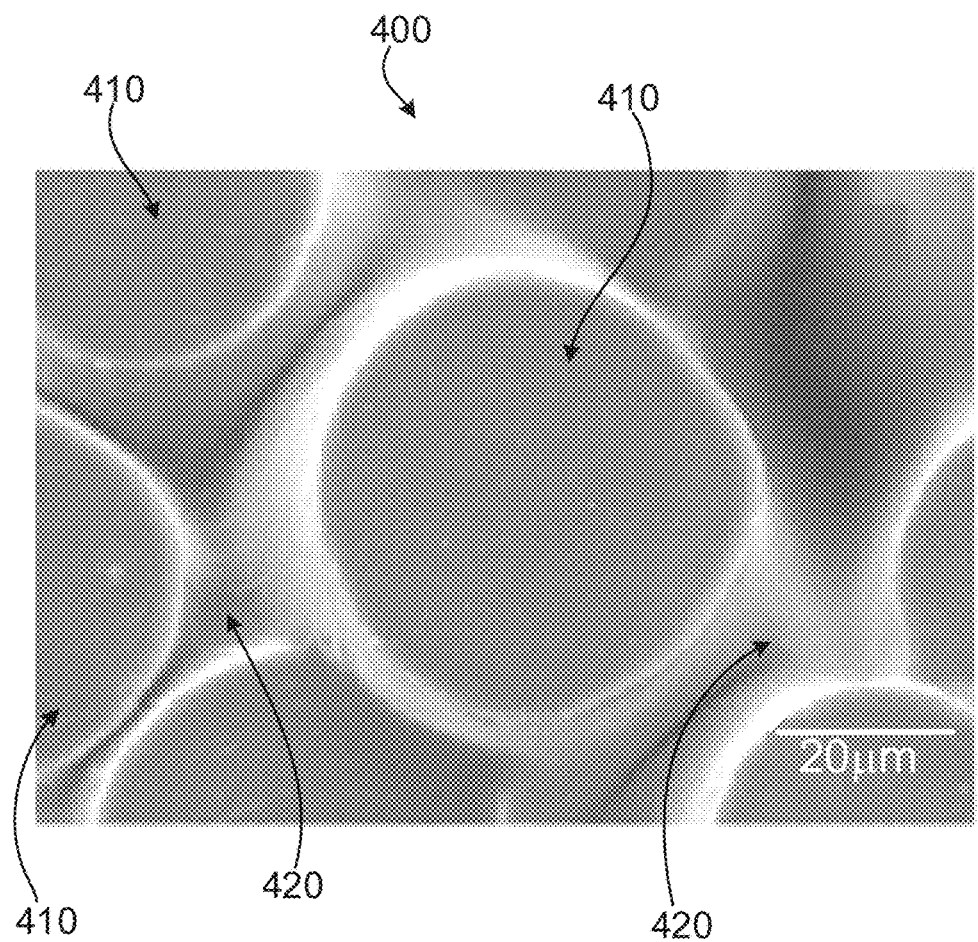
FIG. 4 is a microscope image of a SRC structure provided herein.

FIG. 4 provides an image of an exemplary SRC structure 400 provided herein that is composed of a plurality of fused fibers 410 in which each fused fiber 410 is fused to at least one adjacent fiber by a reflowed fiber domain region 420. The depicted SRC structure 400 shows fibers 410 that have been lightly compacted and heated together. Individual fibers 410, when compressed and heated, can fuse to adjacent fibers by melting at interfacial regions that form reflowed fiber domain regions 420 between the fibers 410. Reflowed fiber domains are portions of a fiber that have re-solidified after having been melted and subsequently cooled. In some cases, the reflowed fiber domain region 420 can be formed when an outer portion of the original fiber is melted and re-solidified. In some cases, the reflowed fiber domain region 420 can adhere a surface of the original fiber to a surface of one or more adjacent fibers, causing the fibers 410 to become fused together. The reflowed fiber domains can, in some cases, flow away from an area of the original fiber, e.g., when an adjacent fiber compresses against a melted outer portion of the original fiber. In some cases, the reflowed fiber domain can fill into a gap (i.e., a pore) that had previously existed between the original fiber and at least one adjacent fiber. As such, the reflowed fiber domain region 420 can fill the gaps that existed between the original fiber and its neighboring fibers to form a plurality of fused fibers 410 with a generally closed pore configuration. In some cases, a SRC structure 400 can have a generally closed pore configuration, meaning that pores (i.e., voids) within the structure do not extend from one side of the structure 400 to an opposite side of the structure 400, i.e., pores do not continuously extend through the entire SRC structure 400.

The SRC structure 400, in some cases, includes reflowed fiber domain regions 420 that are formed from a plurality of fibers 410 of the SRC structure 400. The reflowed fiber domains and the fibers of a SRC structure 400 can therefore, in some cases, be made of a same polymeric material. As used herein, a "same polymeric material" is a term used for two or more materials from the same polymer class, or, more specifically, two or more materials having a number average molecular weight within a ±10% relative standard deviation (RSD). In some cases, the fused fibers of the SRC structures 400 result is a higher tensile strength and/or greater toughness as compared to structures having non-fused fibers. SRC structures can therefore offer the benefit of producing thin leaflets, in some cases, which can be particularly advantageous for valves to be implanted using a TAVR procedure. In some cases, SRC structures can be utilized to form synthetic heart leaflets that can mimic mechanical properties of native leaflets, for example, exhibiting anisotropic properties.

In some cases, the SRC structure 400 can result from compressing fibers of a given diameter, which are aligned in one direction (or arranged in layers of aligned fibers), then compacted while heating near the melting point for a pre-determined amount of time. In some cases, the resultant SRC can include a matrix composed of the same polymers as the fibers since the matrix is generated by melting the outer surface of the fibers therein.

In some cases, the SRC structure 400 is a structure that can arise from placing a first plurality of fibers made of a first polyisobutylene urethane (PIB-PUR) material and a second plurality of fibers made of a second PIB-PUR, the first PIB-PUR and the second PIB-PUR have different molecular weights (MW) and different hard segment to soft segment ratios (HS/SS ratio), and compacting the first and second plurality of fibers at temperatures near the melting point of the lower melting fiber. In some cases, first and second plurality of fibers having different molecular weights or hard segment to soft segment ratios could be placed either parallel to one another in the same layer, or in successive layers. In some cases, the first and second plurality of fibers can be intermingled or separated within a SRC structure 400. In some cases, a SRC structure can includes a layered structure that is formed with a first layer of fibers having a first MW or HS/SS ratio, either parallel to a subsequent second layer of fibers having a second MW or HS/SS ratio, or at an angle to the subsequent second layer of fibers. A SRC structure 400 can include a range of different number of layers of fibers, as desired. For example, a SRC provided herein can include a laminate structure having two layers, three layers, five layers, ten layers, or more than ten layers of fibers, with subsequent layers placed at an angle to the previous layer. In some cases, the number of layers within a SRC structure may be limited by a desired diameter and thickness of a final structure.

Figure 5:
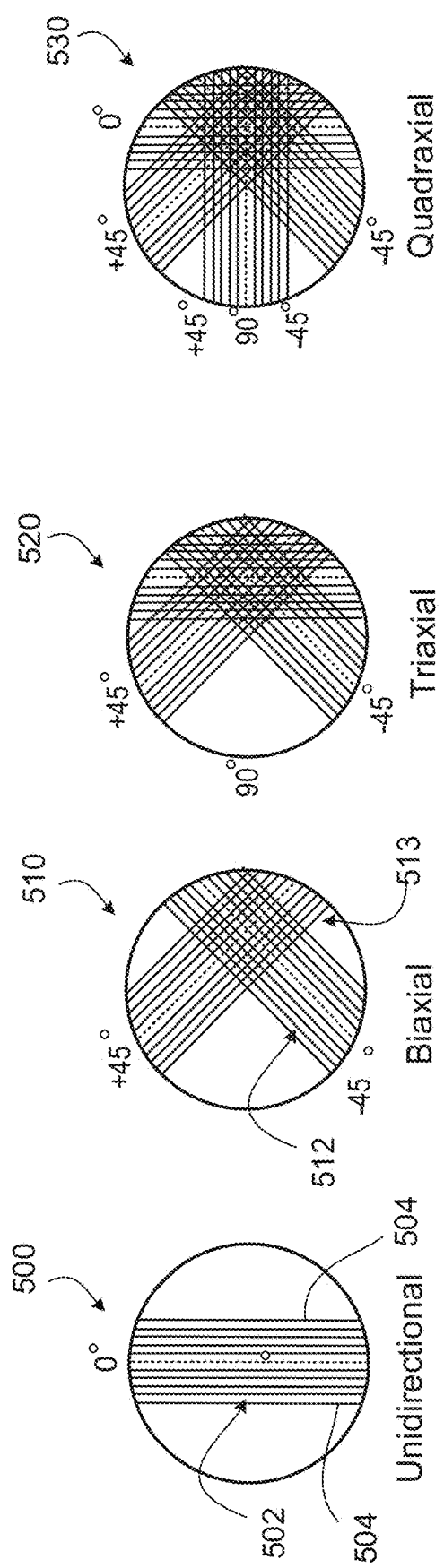
FIG. 5 are schematic illustrations of various orientations of SRC structures provided herein.

Referring to FIG. 5, a SRC structure 500, 510, 520, 530 can include one or more layers in which each layer has a fibrous structure composed of a plurality of fibers. The depicted SRC structures may provide fibers oriented at an angle relative to a radial direction along a heart valve leaflet (e.g., the radial direction along heart valve 300 in FIG. 3). For example, in FIG. 5, 0 degrees can reflect a radial orientation while 90 degrees can reflect a circumferential direction. In some cases, a layer of the SRC structure 500, 510, 520, 530 can include a fibrous structure that has a plurality of aligned, oriented fibers. For example, a depicted unidirectional SRC structure 500 is made of a layer 502 having a plurality of fibers 504 generally oriented in one direction for providing a heart leaflet with anisotropic mechanical properties. In some cases, the plurality of fibers, e.g., fibers 504, can extend along from one edge of a leaflet to an opposite edge of the leaflet. In some cases, the unidirectional SRC structure 500 can include multiple layers in which each layer is composed of fibers made of different or same materials oriented in the one direction. In some cases, the fibrous structure includes a plurality of randomly oriented fibers.

In some cases, the SRC structure 500, 510, 520, 530 can be formed by including one or more layers. In some cases, one layer can be disposed over another layer. For instance, in some cases, a first layer (e.g., layer 502) can be disposed over at least a portion of a second layer. The SRC structures 500, 510, 520, 530 can include one or more layers of SRC structures in which one or more layers have different fiber orientations, in some cases. In some cases, a first and a second layer of the SRC structure can be made of the same materials, but have different fiber orientations. As shown in FIG. 5, SRC structures, such as SRC structure 510, can include a biaxial structure. The biaxial SRC 510 can include a first layer 512 composed of fibers oriented in a first direction and a second layer 513 composed of fibers oriented in a second direction. In some cases, the first direction of the first layer 512 can define a longitudinal axis from which a second direction of the second layer 513 can be oriented, as desired. For example, in some cases, the first direction of the first layer 512 can define a longitudinal axis in which the second direction of the second layer 513 is oriented at an angle orthogonal therefrom. In some cases, the first direction of the first layer 512 can define a longitudinal axis in which the second direction of the second layer 513 is oriented at an angle oblique therefrom. In some cases, the second direction of the second layer 513 is oriented at angle of about 0 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degree, about 65 degrees, about 70 degrees, about 75 degrees, about 80 degrees, about 85 degrees, or about 90 degrees with respect to the longitudinal axis defined by the first direction of the first layer 512. In various cases of the heart valve leaflet described herein, SRC structures can include fibers that include a variance in the angle orientation in the range of plus or minus 2 degrees (i.e., +/−2°) of the stated value, which is signified using the term "about" in describing the material. In some cases, the second direction of the second layer 513 is oriented at angle of about 0 degree to about 10 degrees, about 10 degrees to 20 degrees, from about 20 degrees to 30 degrees, from about 30 degrees to about 40 degrees, from about 40 degrees to about 45 degrees, from about 45 degrees to about 50 degrees, from about 50 degrees to about 60 degrees, from about 60 degrees to about 70 degrees, from about 70 degrees to about 80 degrees, or from about 80 degrees to about 90 degrees with respect to the longitudinal axis defined by the first direction of the first layer 512.

The SRC structure can, in some cases, include a plurality of randomly oriented fibers. A SRC structure composed of a random fiber configuration can provide a highly useable improvement in Young's modulus. For example, in some cases, a SRC structure (e.g., cast films and films) provided herein can include hot compacted fibers for increasing a Young's Modulus by at least about 10%, about 20%, about 30%, about 40%, about 50%, or more than about 50% as compared to structures lacking compacted fibers. In some cases, a SRC structure (e.g., cast films and films) provided herein can include hot compacted fibers for increasing elongation at yield by at least about 10% about 20%, about 30%, about 40%, about 50%, or more than about 50% as compared to a structures that lack compacted fibers. A SRC structure (e.g., cast films and films) provided herein, in some cases, can include a fiber configuration for increasing the ultimate tensile strength by at least about 25%, about 50%, about 60%, about 70%, about 80%, about 100%, or greater than 100% in the direction of fiber alignment, for example, when compared to structures that do not have compacted fibers. In some cases, SRC structures can include fibers having an ordered, aligned configuration. SRC structures that include an aligned, orderly fiber configuration can offer a substantial increase in Young's modulus of a fibrous structure in a particular direction. Aligned fiber configurations can provide high strength in a desired axial direction and anisotropic properties that can increase the robustness of a heart valve leaflet material.

Still referring to FIG. 5, SRC structures 500, 510, 520, 530 can include biaxial 510, triaxial 520 or quadraxial 530 structures. In some cases, SRC structures 510, 520, 530 can be composed of fibers oriented at different angles. In some cases, the fibers (or layers of fibers) of a SRC structure 510, 520, 530 can be oriented at different angles. For example, as shown in FIG. 5, a triaxial SRC 520 can include a first plurality of fibers having a first direction and a second plurality of fibers having a second direction at a first angle and a third plurality of fibers having a third direction at a second angle. In some cases, for example, a triaxial SRC 520 can include a first layer composed of a SRC material having fibers oriented in a first direction and defining a longitudinal axis, a second layer composed of a SRC material having fibers oriented in a second direction of about 45 degrees from the longitudinal axis, and a third layer composed of a SRC material having fibers oriented in a second direction of about 90 degrees from the longitudinal axis. Still referring to FIG. 5, in some cases, a quadraxial SRC 530 can include a first plurality of fibers having a first direction, a second plurality of fibers having a second direction at a first angle, a third plurality of fibers having a third direction at a second angle, and a fourth plurality of fibers having a fourth direction at a third angle.

In some cases, at least two layers of the multilayered SRC 510, 520, 530 can be oriented at the same or different angle with respect to one another. In some cases, the SRC structure can include more than five layers, for example, a quinaxial SRC structure (not shown). In some cases, fibers can be placed in a desired orientation within the SRC structure 500, 510, 520, 530 to increase and/or maximize the mechanical properties in a particular direction in the leaflet provided herein. By including multiple layers having different fiber orientations in a SRC structure 500, 510, 520, 530, mechanical properties of the SRC structure 500, 510, 520, 530 can be modified as desired in different directions.

A SRC structure, in some cases, is a laminate structure that can include two layers, three layers, five layers, ten layers, or more than ten layers of fibers made of 2 or more distinct polymers. For example, in some cases, first and second layers of a SRC structure 500, 510, 520, 530 can be made of different, but heat-fusible, compatible materials (e.g., compatible polymeric materials). The first and second layers can be oriented to have the same fiber orientation, in some cases. An exemplary SRC, in some cases, can include a first layer composed of a SRC structure 500, 510, 520, 530 made of polyurethane that can be heat fused to a second layer composed of a SRC structure 500, 510, 520, 530 made of a polyamide. In some cases, first and second layers of a SRC structure 500, 510, 520, 530 can be made of the same material, but have different physical properties. For example, in some cases, a prosthetic heart leaflet material can include a first layer composed of a SRC structure 500, 510, 520, 530 made of a first polyurethane and a second layer composed of a SRC structure 500, 510, 520, 530 made of a second polyurethane having a lower durometer than the first polyurethane.

Figure 6A:
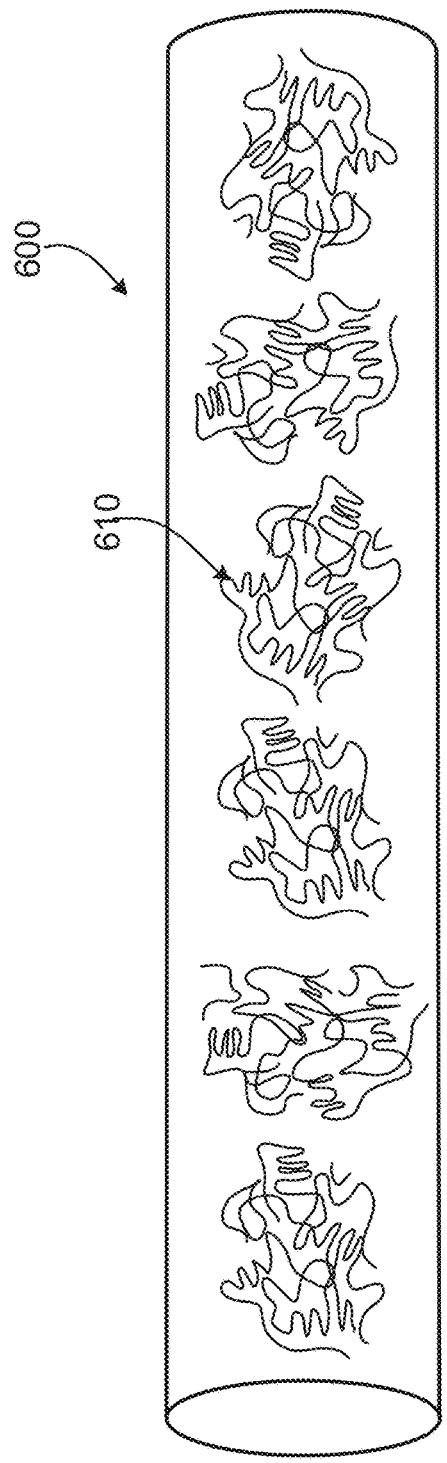
FIGS. 6A and 6B are schematic illustrations of crystal orientations of fibers of a SRC structure provided herein.
Figure 6B:
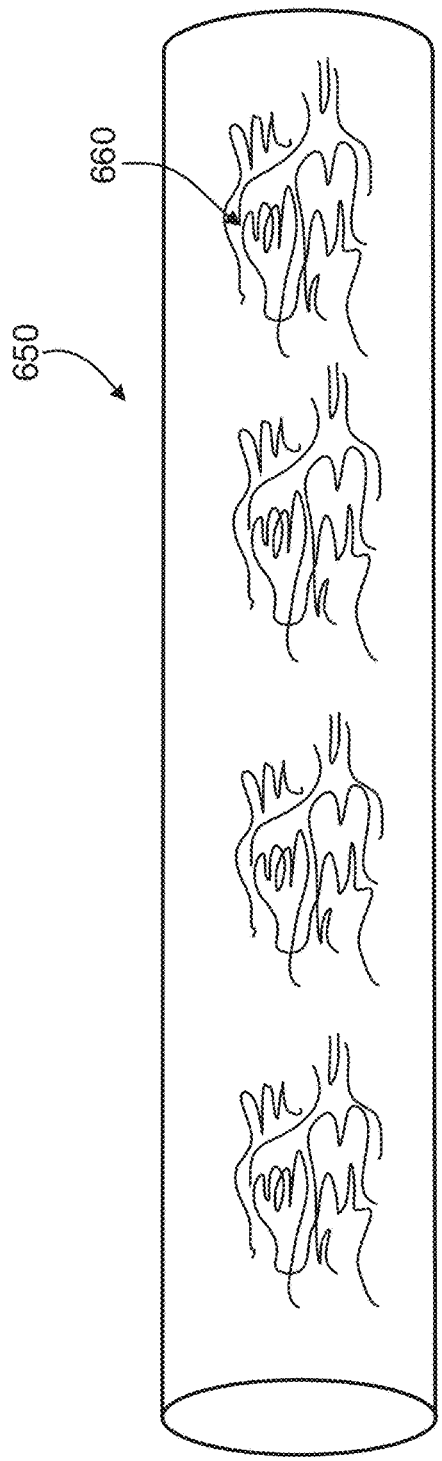

Referring to FIGS. 6A and 6B, each fiber 600, 650 of a SRC structure (e.g., SRC structure 500, 510, 520, 530 of FIG. 5) provided herein can be made of a polymeric material composed of a plurality of polymer crystals 610, 660. Polymer crystals 610, 660 are regions of three-dimensional ordering formed by intramolecular folding and/or stacking of adjacent polymeric chains. In some cases, as shown in FIG. 6A, an individual fiber 600 can be composed primarily of amorphous domains, or randomly oriented polymer crystals 610. In some cases, as shown in FIG. 6B, an individual fiber 650 can be composed primarily of crystalline or semi-crystalline domains, for example, aligned crystals 660 that are oriented in one direction. In some cases, the individual fiber 650 can include aligned crystals 660 oriented in two or more directions. For instance, in some cases, each fiber 650 can include crystals 660 configured in a uniaxial, biaxial, triaxial, or quadraxial orientation. In some cases, fibers 600, 650 can be oriented within a SRC structure such that the crystal structure of individual fibers 600, 650 are aligned to increase and/or maximize the mechanical properties in a particular direction in the heart valve leaflets provided herein.

SRC structures (e.g., fibers and reflowed fiber domain regions) provided herein can be composed of various polymeric materials. In various cases, a SRC structure, for example, fibers (e.g., fiber 600, 650), can be made of a medically suitable polymeric material. Suitable polymeric materials can include, but are not limited to, polypropylenes, polyesters, polytetrafluoroethylenes (PTFE) such as TEFLON® by E. I. DuPont de Nemours & Co., polyethylenes, polyurethanes, polyamides, nylons, polyetheretherketones (PEEK), polysulfones, fiberglass, acrylics, tantalum, polyvinyl alcohols, carbon, ceramics, metals (e.g., titanium, stainless steel), and combinations thereof. In some cases, suitable polymers for forming SRC can be made from polyurethanes, for example, polyisobutylene urethanes (PIB-PUR), polyurethane elastomers (e.g. Pellethane), polyether-based polyurethanes (e.g. Tecothane), polycarbonate-based polyurethanes (e.g. Bionate and/or Chronoflex) and combinations thereof. Some examples of suitable polymer materials for SRC structures include, but are not limited to, polycarbonate, polyether, polyester, polyamide, nylon 6, nylon 12, polyetherimide and combinations thereof. In some cases, SRC structures can be made of a silk-based biomaterial. Silk-based biomaterials can include materials constructed from silk proteins such as silkworm fibroin, spider fibroin or *Bombyx mori* silk fibroin. In some cases, SRC structures can be composed of silk-like materials such as fibronectin, elastin, or other silk-like proteins, for example, aneroin which is a protein derived from the sea anemone *Nematostella vectensis*.

In some cases, fibers and reflowed fiber domain regions within the SRC material of a leaflet (e.g., leaflet 300 of FIG. 3) provided herein can be made of a liquid crystalline polymer (LCP). LCPs are a special class of aromatic polyester and/or polyamide copolymers that have semi-crystalline properties due to regions of highly ordered crystalline structures formed therein. Suitable fiber materials made of LCPs include, but are not limited to, thermotropic polyester such as Vectran®, poly(p-phenylene terephthalamide) (PPTA), and poly(phenylene benzobisoxazole) (PBO) and combinations thereof. Well-known LCPs include Kevlar®, Vectran®, Nomex®, Herachron®, Technora®, Twaron®, and Zylon®. In some cases, high performance fibers can be utilized in composite materials, such as gel-spun ultra-high molecular weight polyethylene (Dyneema®).

LCPs are generally chemically inert and have a high creep resistance, a high modulus and a high tensile strength. LCPs provide the advantage of using materials with thinner and smaller dimensions, e.g., layer thickness or fiber diameter, without compromising strength, robustness and durability. In some cases, the diameter of LCP fibers can be as small as 0.5 micrometers (microns), or about 0.00002 inches, and a total thickness of a leaflet (e.g., leaflet 300 of FIG. 3) provided herein that are composed of LCP fibers can be as thin as about 50 microns to about 100 microns (or about 0.002 to about 0.004 inches).

In some cases, SRC structures (e.g., the fibers and the reflowed fiber domain regions of a SRC structure) be made of an elastomeric polymer. Suitable fibers and the reflowed fiber domain regions include, but are not limited to, homopolymers, copolymers and terpolymers. Various polyurethanes can be used to construct the fibers and the reflowed fiber domain regions, such as polyurethanes with soft segments such as polyether, perfluoropolyether, polycarbonate, polyisobutylene, polysiloxane, or combinations thereof. Polyurethane hard segments can include, but are not limited to, methylene diphenyl diisocyanate (MDI), 4,4'-Methylene dicyclohexyl diisocyanate (H12MDI) and hexamethylene (HMDI). In some embodiments, the polymer matrix can be formed from block polymers such as, for example, poly(styrene-isobutylene-styrene) (SIBS) tri-block polymers. Some suitable elastomeric materials include, but are not limited to, silicones, nitrile rubber, fluoroelastomers, polyolefin elastomers, latex-type elastomers, various natural elastomers such as those made from collagen, elastin, cellulose, proteins, carbohydrates and combinations thereof.

Leaflets provided herein (e.g., leaflet 300 of FIG. 3) can include SRC composite structures having original (i.e., pre-fused) fiber diameters that can range from about 10 nanometers (nm) to about 100 nm, from about 100 nm to about 50,000 nm or 50 micrometers, or from about 0.5 microns to about 200 microns (or about 0.00002 inches to about 0.0079 inches). In some cases, fibers can have original diameters or average diameters of at least 1 micron (or 0.00004 inches). Pre-fused fibers can be, in some cases, in the range of about 1 micron to about 100 microns (or about 0.00004 inches to about 0.004 inches), including all ranges and values therebetween. In some cases, for example, suitable original fiber diameter sizes can include ranges of about 1 micron to 5 microns (or about 0.00004 inches to about 0.0002 inches), 5 microns to 10 microns (or 0.0002 inches to about 0.0004 inches), 10 microns to 20 microns (or 0.0004 inches to about 0.0008 inches), 20 microns to 50 microns (or 0.0008 inches to about 0.0020 inches), and 50 microns to 100 microns (or 0.002 inches to about 0.004 inches). In some cases, original fibers can have diameters in the range of about 1 microns to about 10 microns (or 0.00004 inches to about 0.0020 inches), including all ranges and values therebetween. In some cases, the pre-fused fiber made from polymers can range from about 5 microns to about 100 microns (or 0.00002 inches to about 0.0040 inches), from about 10 microns to about 75 microns (or 0.0004 inches to about 0.003 inches), from about 10 micron to about 50 microns (or 0.0004 inches to about 0.0020 inches), from about 20 microns to about 100 microns (or 0.0008 inches to about 0.0040 inches), from about 25 microns to about 200 microns (or 0.001 inches to about 0.008 inches), or from about 20 microns to about 50 microns (or 0.0008 inches to about 0.002 inches). In some cases, pre-fused fibers, such as LCP fibers, can range from 0.5 microns (or 500 nanometers) to 5 microns (or about 0.00002 inches to about 0.00020 inches).

Leaflets provided herein (e.g., leaflet 300 of FIG. 3) can include SRC composite structures having original (i.e., pre-fused) fibers that are circular in cross sectional shape, or square, or oval, or hexagonal, or some other shape. In some cases, the cross-sectional shape of the fibers of a SRC composite structure can be different before and after fusing. For example, in some cases, a SRC composite structure having original (i.e., pre-fused) fibers with a circular cross-sectional shape can have post-fused fibers with a non-circular cross-sectional shape, such as a rectangular or oval shaped cross-sectional shape.

Figure 7:
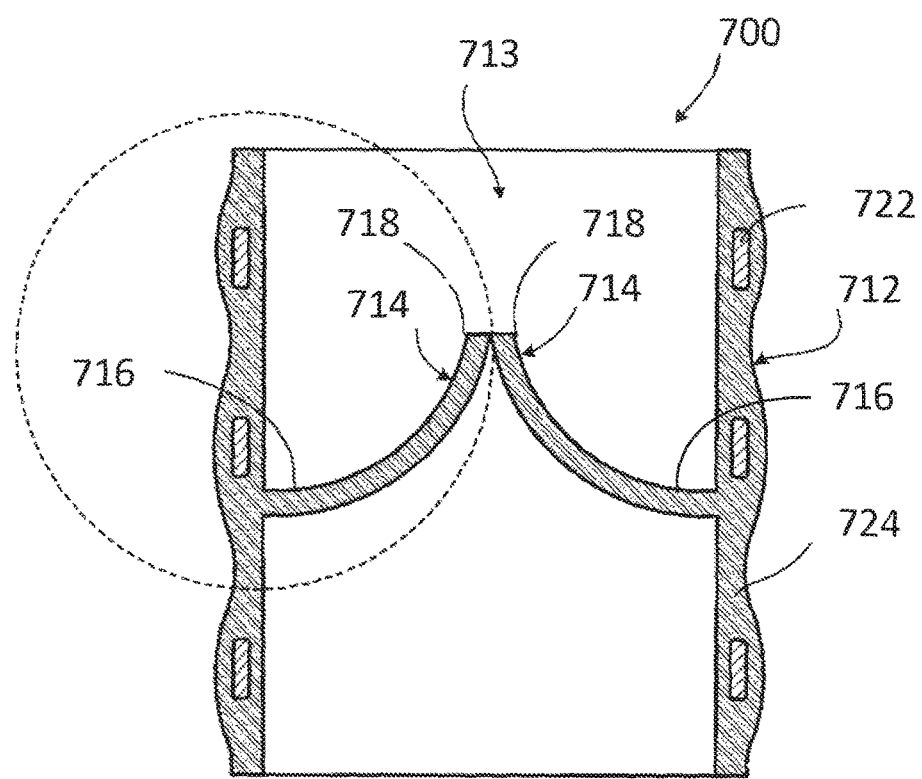
FIG. 7 is an illustration of another exemplary prosthetic heart valve provided herein.

FIG. 7 provides another embodiment of a prosthetic heart valve 700. Prosthetic heart valve 700 includes a base 712 defining a substantially cylindrical passage 713 and a plurality of polymeric leaflets 714 disposed along the substantially cylindrical passage 713. Each polymeric leaflet 714 includes a respective root portion 716 coupled to base 712 and a respective edge portion 718 movable relative to the root portion 716 to coapt with the edge portions of the other polymeric leaflets along a coaptation region. In some cases, the entire heart valve 700 can be made of a composite material provided herein. In some cases, portions of heart valve 700, e.g., the polymeric leaflets 714 of the heart valve 700, can be made of composite materials provided herein. In some cases, the polymeric leaflets 714 can include SRC structures provided herein.

Base 712 includes a frame 722 disposed in a polymer layer 724. The polymer layer 724 can be composed of composite materials provided herein. In some cases, polymer layer 724 can include a SRC structures provided herein. Polymer layer 724 secures respective root portions 716 of polymeric leaflets 714 to the base 712. Polymer layer 724 can form a substantially continuous surface with respective root portions 716 of polymeric leaflets 714. This can reduce the likelihood of stress concentrations at the junction of respective root portions 716 and base 712. Additionally or alternatively, polymer layer 724 can be disposed between each of polymeric leaflets 714 and frame 722 such that polymer layer 724 protects polymeric leaflets 714 from inadvertent contact with frame 722 (e.g., as can occur through eccentric deformation of prosthetic heart valve 700 on a calcium deposit present at the implantation site).

In some cases, frame 722 is substantially cylindrical such that the outer surface of the base 712 is substantially cylindrical and the polymer layer 724 disposed on the frame 722 forms the substantially cylindrical passage 713. In some cases, frame 722 is completely disposed in the polymer layer 724, with the polymer layer 724 forming a contoured outer surface of the valve 700. In some cases, the frame 722 is partially disposed in the polymer layer 724. In some cases, the polymer layer 724 is applied to the frame 722 to form a substantially smooth inner and/or outer surface of the valve 700.

Although the prosthetic heart valves provided herein are generally made of synthetic materials, such as SRC structures, in some cases, prosthetic heart valves can be made of both synthetic materials and non-synthetic materials such as animal tissue. For example, in some cases, at least a portion of a leaflet provided herein can be made from SRC structures provided herein as well as tissue obtained from an animal, e.g., bovine pericardium or porcine tissue.

Methods of Forming Self-Reinforced Composite Structures

Various methods can be utilized to form SRC structures provided herein. For example, in some cases, a method for forming the prosthetic heart valves provided herein includes, but is not limited to, the use of hot compaction. In some cases, a hot compaction process can be applied to form SRC structures provided herein. In some cases, hot compaction is utilized to form synthetic heart leaflets that can mimic mechanical properties of native leaflets, for example, exhibiting anisotropic properties.

Referring back to FIG. 4, which provides an image of an exemplary SRC structure 400 provided herein, fibers 610 can be lightly compacted and heated together to fuse adjacent fibers together. Individual fibers 410, when compressed and heated, can melt interfacial regions that form reflowed fiber domain regions 420 between the fibers 410.

In some cases, SRC structures provided herein can be formed by compressing and heating a fibrous structure to a predetermined temperature for a predetermined amount of time to fuse the fibers without compromising the crystal orientation of individual fibers of the fibrous structure. A suitable predetermined temperature can range between a glass transition temperature (Tg) and the melting point temperature (Tm) of a fiber material. In some cases, the predetermined temperature can be near a melting point temperature, for example, about ±1 degree Celsius of the melting point temperature, about ±5 degrees Celsius of the melting point temperature, about ±10 degrees of the melting point temperature, or about ±15 degrees Celsius of the melting point temperature, about ±20 degrees Celsius of the melting point temperature, or about ±50 degrees Celsius of the melting point temperature. The predetermined temperature can be just above the melting point temperature, for example, in some cases, about 1 degree Celsius, 3 degrees Celsius, 5 degrees Celsius, 7 degrees Celsius, 10 degrees Celsius, 15 degrees Celsius, 20 degrees Celsius, 25 degrees Celsius, 30 degrees Celsius, 35 degrees Celsius, 40 degrees Celsius, 45 degrees Celsius, or 50 degrees Celsius above the melting temperature of a fiber material. In some cases, the fibrous structure is heated to a temperature ranging from about 1 degree Celsius to 5 degrees Celsius, about 5 degrees Celsius to about 7 degrees Celsius, about 7 degrees Celsius to about 10 degrees Celsius, about 10 degrees Celsius to about 15 degrees Celsius, about 15 degrees Celsius to about 20 degrees Celsius, about 20 degrees Celsius to about 25 degrees Celsius, about 25 degrees Celsius to about 30 degrees Celsius, about 30 degrees Celsius to about 35 degrees Celsius, about 35 degrees Celsius to about 40 degrees Celsius, about 40 degrees Celsius to about 45 degrees Celsius, about 45 degrees Celsius to about 50 degrees Celsius, or greater than 50 degrees Celsius above or below the melting temperature of the polymer.

In some cases, the fibrous structure is compressed and heated from about 1 minute (min) to about 180 minutes, including any values or ranges therebetween. In some cases, the fibrous structure is compressed and heated from about 1 minute (min) to about 30 minutes, about 30 minutes to about 60 minutes, about 60 minutes to about 90 minutes, about 90 minutes to about 120 minutes, about 120 minutes to about 150 minutes, about 150 minutes to about 180 minutes. In some cases, the fibrous structure is compressed and heated from about 1 minute (min) to about 5 minutes, about 5 minutes to about 10 minutes, about 10 minutes to about 15 minutes, about 15 minutes to about 20 minutes, about 20 minutes to about 30 minutes, about 30 minutes to about 40 minutes, about 40 minutes to about 50 minutes, about 50 minutes to about 60 minutes, about 60 minutes to about 90 minutes, about 90 minutes to about 120 minutes, about 120 minutes to about 150 minutes, about 150 minutes to about 180 minutes, or greater than 180 minutes.

In some cases, the fibrous structure is compressed with a pressure ranging from about 0.1 tons (about 91 kilograms) to about 10 tons (9,071 kilograms) of pressure, including all values and ranges therebetween.

In some cases, the hot compaction process includes using a predetermined temperature that can range from a glass transition temperature (Tg) and a melting temperature (Tm) of the fiber material. In some cases, a compressional strain percentage ranging from about 0% to about 50% is applied to a plurality of fibers of the fibrous structure during the compressing and the heating steps of the hot compaction process.

SRC structures can, in some cases, include "melt regions" between fibers of the structure. In some cases, the melt regions can be formed when portions of the fibers melt and fuse to adjacent fibers and/or melt regions. In some cases, the melt regions can fuse the fibers of the SRC structure together. As the SRC structure cools, its melt regions can recrystallize into a different structure or remain in a same or similar structure as compared to pre-melted fibrous structure, in some cases. For example, in some cases, a SRC structure can include melt regions that recrystallize into an amorphous structure that was existent in the fibrous structure prior to the melt processing.

The melt processing provided herein, in some cases, yields a SRC structure that fuses each fiber with its neighboring, adjacent fibers. Benefits of the resultant SRC structure can include increasing the strength of the material by producing highly aligned crystalline fibers and/or enhancing material toughness due to fused interfiber regions. In some cases, hot compaction processing can enable the use of a wide selection of material compositions and fiber alignments for producing a synthetic leaflet capable of more closely mimicking native leaflet properties.

There are several methods that can be used to achieve the initial fiber alignment and resultant fused SRC structure. Suitable methods can include, but are not limited to, an injection molding, uniaxial or biaxial pressing, isostatic pressing, slip casting, or extrusion molding process. Suitable methods can, in some cases, include an overheating method or a film stacking method, as will be discussed herein.

An overheating method can be used to create a large enough processing window for creating SRC structures. In the overheating method, fibers are embedded into a molten reflowed fiber domain regions composed of the same material as the fibers. The fibers are constrained while being embedded into the molten reflowed fiber domain regions, e.g., constrained in a fibrous structure, such that the melting temperature of the fibers shift to a higher melting temperature. Polymer fibers can be overheated above their melting temperature when the fibers are constrained. The overheating method provides the benefit of preventing or minimizing shrinkage during processing of the resultant SRC structure.

A film stacking method is a method that hot presses together a fibrous structure (which can also be described as a reinforcing textile structure) placed between two matrix films. Suitable materials that can be used when applying the film stacking method include, but are not limited to, nylon such as aramid, polypropylene (PP), polyethylene (PE), ultra-high-molecular-weight polyethylene (UHMWPE), polylactic acid (PLA), and isotactic polypropylene (iPP) fibers. Advantages of the film-stacking method include the use of a wide processing window, freedom of the material selection, and simplified manufacturing.

In some cases, an initial SRC structure can be formed and then subsequently laminated with additional fibers (or layers of fibers) in successive layers that are deposited in a non-parallel arrangement. Multiple layers could be built up in this manner prior to compaction.

SRC structures can be made, in some cases, by using two or more polymer types. In some cases, an exemplary SRC structure can be formed by producing a pre-cursor structure composed of a biodegradable material (e.g., polylactic acid) and a non-biodegradable material (e.g., polyurethane). In some cases, the fibers and/or portions of the reflowed fiber domain regions are composed of the non-biodegradable material. In some cases, a portion of the fibers and/or reflowed fiber domain regions are composed of the biodegradable material. The exemplary SRC can be formed when the biodegradable material degrades, leaving the non-biodegradable material behind. The resultant exemplary SRC structure includes a porous composite composed of fibers fused together with reflowed fiber domain regions made of the same material as the fibers.

In some cases, a SRC structure can be made using two or more materials composed of a same base material, but having different physical properties, e.g., different melting points. For example, in some cases, an exemplary SRC structure can include a first plurality of fused fibers made of a high-melt-temperature polyurethane and a second plurality of fused fibers are made of a low-melt-temperature polyurethane. The reflowed fiber domain regions can be composed of the low-melt-temperature polyurethane, the high-melt-temperature polyurethane or both, in some cases.

The SRC structure provided herein can be formed with aligned polymer crystals oriented in one or more directions. Suitable methods of orienting crystals in a self-reinforced composite include, but are not limited to, extruding, drawing, and rolling. For instance, in some cases, extruding, drawing or rolling fibers can align polymer molecules and/or polymer crystals within each fiber, thus increasing or maximizing crystal alignment of the resultant self-reinforced composite. In some cases, optimizing process parameters can maximize crystal alignment, for example, parameters such as solvent selection and composition, drying time and target distance in electrospinning.

We claim:

1. A prosthetic heart valve leaflet comprising
a self-reinforced composite (SRC) structure comprising
a first layer comprising a first plurality of fused fibers composed of a first polymeric material and characterized by each fiber being fused to at least one adjacent fiber by a reflowed fiber domain region; and
a second layer comprising a second plurality of fused fibers composed of a second polymeric material and characterized by each fiber being fused to at least one adjacent fiber by a reflowed fiber domain region;
wherein the first and second polymeric materials are different materials.

2. The prosthetic heart valve leaflet of claim 1, wherein the first plurality of fused fibers and the second plurality of fused fibers are generally aligned in at least two directions such that the first plurality of the fused fibers are oriented at a first predetermined fiber angle relative to the second plurality of fused fibers.

3. The prosthetic heart valve leaflet of claim 2, wherein the predetermined fiber angle is an orthogonal angle.

4. The prosthetic heart valve leaflet of claim 2, wherein the predetermined fiber angle can range from about 10 degrees to 20 degrees, from about 20 degrees to 30 degrees, from about 30 degrees to about 40 degrees, from about 40 degrees to about 45 degrees, from about 45 degrees to about 50 degrees, from about 50 degrees to about 60 degrees, from about 60 degrees to about 70 degrees, from about 70 degrees to about 80 degrees.

5. The prosthetic heart valve leaflet of claim 1, wherein the first plurality of fused fibers are generally aligned in a direction defining a first longitudinal axis, the first longitudinal axis being oriented at an angle relative to a free edge of the prosthetic heart valve leaflet.

6. The prosthetic heart valve leaflet of claim 5, wherein each fiber of the first plurality of fused fibers comprises an aligned polymer crystal orientation that is generally parallel with the first longitudinal axis.

7. The prosthetic heart valve leaflet of claim 1, wherein the first layer is disposed adjacent to the second layer.

8. The prosthetic heart valve leaflet of claim 1, wherein the first plurality of fused fibers of the first layer are oriented in a first direction and the second plurality of fused fibers of the second layer are oriented in a second direction to form a biaxial orientation within the SRC structure.

9. The prosthetic heart valve leaflet of claim 1, wherein the SRC structure comprises additional layers to form a three-, four-, or a five-composite-layered SRC structure.

10. The prosthetic heart valve of claim 9, wherein the three-, four- or five-composite-layered of the SRC structure forms a triaxial, a quadaxial or a quinaxial orientation, respectively.

11. The prosthetic heart valve leaflet of claim 1, wherein the first polymeric material is a polyurethane, a polyisobutylene urethane (PIB-PUR) copolymer, a polyamide, a polyimide, a polycarbonate, a polyester, a polyetherether ketone, or a fluorinated polyolefin.

12. The prosthetic heart valve leaflet of claim 1, wherein the first polymeric material is a high-melt-temperature polyurethane and second polymeric material is a low-melt-temperature polyurethane.

13. The prosthetic heart valve leaflet of claim 1, wherein the first layer at least partially overlaps the second layer.

14. The prosthetic heart valve leaflet of claim 1, wherein at least a portion of the first layer is fused to at least a portion of the second layer.

15. The prosthetic heart valve leaflet of claim 1, wherein each fiber of the first plurality of fibers has a generally square, oval, or hexagonal cross-sectional shape.

* * * * *